United States Patent [19]

Lederman et al.

[11] Patent Number: 4,888,009
[45] Date of Patent: Dec. 19, 1989

[54] PROSTHETIC HEART VALVE

[75] Inventors: David M. Lederman, Marblehead; Param I. Singh, Lexington; Clair L. Strohl, Jr., Norfolk, all of Mass.

[73] Assignee: Abiomed, Inc., Danvers, Mass.

[21] Appl. No.: 926,816

[22] Filed: Oct. 31, 1986

Related U.S. Application Data

[63] Continuation of Ser. No. 720,361, Apr. 5, 1985, abandoned.

[51] Int. Cl.⁴ .............................................. A61F 2/24
[52] U.S. Cl. .......................................... 623/2; 623/900
[58] Field of Search ...................................... 623/2, 900

[56] References Cited

U.S. PATENT DOCUMENTS

| | | | |
|---|---|---|---|
| 3,279,996 | 10/1966 | Long, Jr. et al. | 623/2 X |
| 3,320,972 | 5/1987 | High et al. | 623/2 X |
| 3,589,392 | 6/1971 | Meyer . | |
| 3,744,060 | 7/1973 | Bellhouse et al. | 623/2 |
| 4,035,849 | 7/1977 | Angell et al. . | |
| 4,079,468 | 3/1978 | Liotta et al. | 623/2 |
| 4,222,126 | 9/1980 | Boretos et al. | 3/1.5 |
| 4,364,127 | 12/1982 | Pierce et al. | 623/2 |
| 4,473,423 | 9/1984 | Kolff | 623/2 X |
| 4,624,822 | 11/1986 | Arru et al. | 623/2 X |

FOREIGN PATENT DOCUMENTS

| | | |
|---|---|---|
| 0155245 | 9/1984 | European Pat. Off. . |
| 0143246 | 9/1985 | European Pat. Off. . |

Primary Examiner—Alan W. Cannon
Attorney, Agent, or Firm—Nutter, McClennen & Fish

[57] ABSTRACT

A prosthetic heart valve comprises a suture ring supporting a stent which surrounds a conduit bearing a plurality of flexible valve leaflets. The conduit extends beyond the end of the suture ring.

1 Claim, 1 Drawing Sheet

PROSTHETIC HEART VALVE

This application is a continuation of application Ser. No. 720,361, filed Apr. 5, 1985, now abandoned.

BACKGROUND OF THE INVENTION

This invention relates generally to prosthetic heart valves for replacement of diseased or damaged natural heart valves, and relates particularly to prosthetic heart valves which use flexible leaflets of synthetic material which mutually coapt to permit flow in only one direction, somewhat like natural valves. Such valves can provide good flow performance with little disturbing noise or vibration, but were initially considered not to have sufficient durability. This deficiency now seems to have been remedied by development of better synthetic materials and methods of assembly, together with designs which permit suitably low cyclic strain on the flexible material.

With the foregoing problems in hand, a further problem has appeared: chronic thrombus formation and actual tissue overgrowth, particularly around the upstream end of the prosthetic valve, occurs far too often.

SUMMARY OF THE INVENTION

It is accordingly the principal object of the invention to produce a prosthetic valve, of the class described, which does not exhibit the deficiency of chronic thrombus formation and tissue overgrowth. According to this invention, our valve is provided with a conventional fabric suture ring to affix the valve to the heart by sutures and eventual tissue ingrowth, and also with a central conduit, of smooth synthetic material of low thrombogenicity and tissue reactivity, which extends beyond the suture ring, particularly in the upstream direction, so that the blood flow is not exposed to the region of thrombogenesis and tissue reaction at and within the suture ring, thus avoiding provoking chronic thrombus formation and tissue overgrowth. Other objects of this invention, as well as the means for attaining them, are set forth in the accompanying Specification and Drawings, wherein:

DETAILED DESCRIPTION OF THE INVENTION

Figure 1:
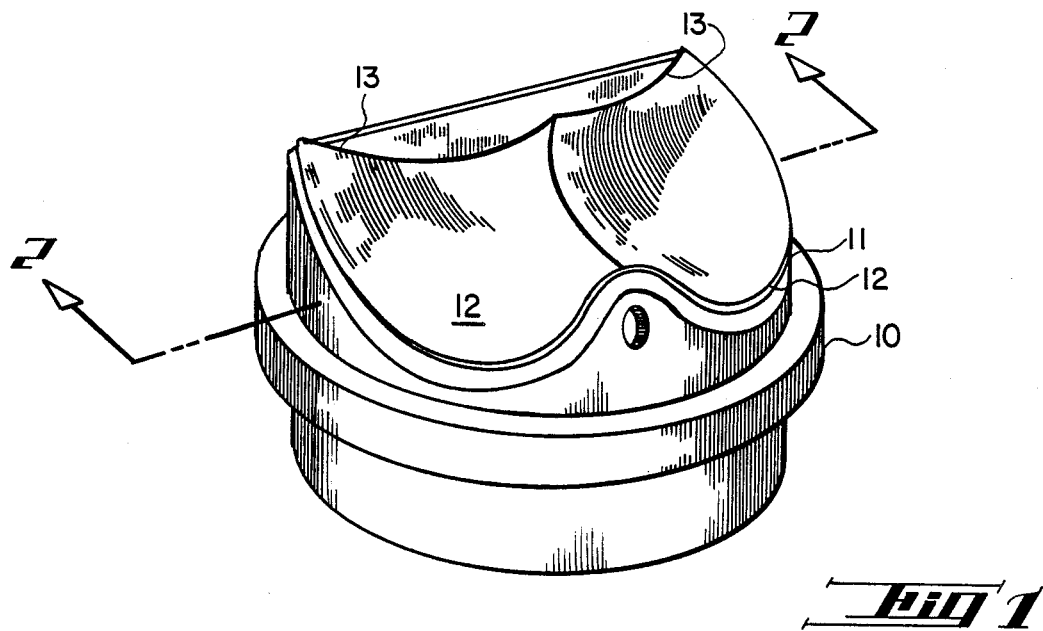
FIG. 1 is an exterior perspective view of a closed prosthetic valve according to the invention.

As shown in FIG. 1, the valve comprises a suture ring 10 of synthetic fabric material surrounding a generally cylindrical body 11 bearing curved flexible leaflets 12 which abut each other along coaptation lines 13 when the valve is closed. The downstream end of the valve is toward the top of the drawings.

Figure 2:
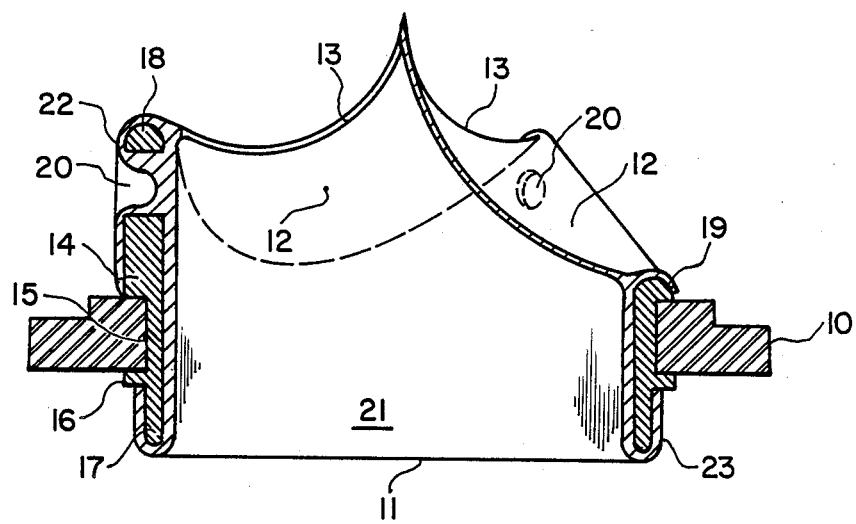
FIG. 2 is a sagittal cross-section of that valve in the direction indicated by 2—2 in FIG. 1.
Figure 3:
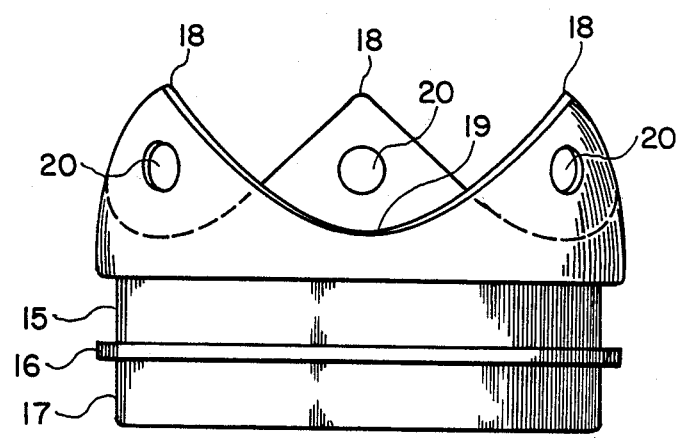
FIG. 3 is an elevational view of a stent which is a component of that valve.

Referring now to FIG. 2, it is seen that body 11 comprises a stent 14, preferably of polished stainless steel, shown separately in FIG. 3. Stent 14 bears a groove 15 and a flange 16 for engaging suture ring 10, and preferably has an upstream collar 17 extending beyond the upstream face of suture ring 10. Stent 14 also has peaks 18 extending in a downstream direction, alternating with valleys 19; peaks 18 are provided with fenestrations 20.

Referring again to FIG. 2, it is seen that body 11 also comprises a conduit 21, of flexible polymeric material, which lines the interior of stent 14, abuts the downstream end of the stent and preferably passes around the upstream end of the stent and then around the outer surface of the stent toward the upstream face of the suture ring. Conduit 21 is integrally joined with leaflets 12 which are preferably composed of the same flexible polymeric material.

Many flexible polymeric materials suitable for contact with blood exhibit feeble bonding to smooth hard materials such as polished metals. This permits convenient removal of such materials from polished production mandrels, but presents an assembly problem if one wishes to avoid use of rough surfaces or reactive priming materials. Therefore, we prefer to affix conduit 21 to stent 14 by integrally bonding additional flexible polymeric material to the downstream end of conduit 21 to provide an outer coating 22 on the outer wall of the downstream end of stent 14, extending toward the downstream face of suture ring 10, and reaching through fenestrations 20 to bond integrally with conduit 21.

The described structure may be assembled as follows: the required flexible polymeric material is dissolved in a volatile solvent to form a homogeneous syrupy polymer solution. A highly-polished conduit mandrel, having a narrower portion of diameter slightly greater than that of the inside of the desired conduit and a wider portion beginning along a contour following the peaks and valleys of a stent, is repeatedly dipped in the polymer solution with interspersed drying periods, to form an extended conduit of about 0.3 mm thickness; this is stripped from the mandrel.

A highly-polished leaflet mandrel, matching the contour of the upstream side of the closed leaflets, is inserted into the narrower portion of the extended conduit and carefully aligned. Polymer solution is then poured into the wider portion of the extended circuit, and the assembly is rotated slowly while the solution dries, forming thin leaflets of flexible polymeric material integrally joined to the inside of the conduit. This process is repeated until the leaflets are about 0.4 mm thick. The conduit-leaflet assembly is stripped from the leaflet mandrel, and most of the wider portion of the conduit, downstream from the leaflets, is trimmed away, leaving only a narrow outwardly-directed ruff about 0.6 mm wide.

Stent 14 is given a thin coating of the flexible polymeric material about 0.14 mm thick (not shown in the drawings). The stent is then slipped over the conduit and aligned to abut the narrow ruff. Polymer solution is employed to bond the ruff to the stent coating and to bond the conduit to the stent coating through fenestrations 20. While the abutment of the ruff upon the downstream end of stent 14 provides substantial axial support, we prefer to add sufficient coats of polymer solution to provide an outer coating 22 about 0.4 mm thick, extending the ruff toward the downstream face of suture ring 10, and bonded to conduit 21 through fenestrations 20.

The upstream end of conduit 21 is cut to length, everted over collar 17 to form cuff 23 and bonded to the stent coating with polymer solution. Suture ring 10 may then be added, and the leaflets separated from each other along coaptation lines 13.

To avoid chronic thrombus formation and tissue overgrowth at the upstream end of the valve, conduit 21 should extend at least 1.5 mm farther upstream than the upstream face of suture ring 10, and preferably at least 3.0 mm; in the preferred embodiment described and illustrated, this extension is about 3.6 mm. Likewise, to avoid these deficiencies at the downstream end of the valve, the ruff of conduit 21 and outer coating 22 should extend at least 1.0 mm farther downstream than the downstream face of suture ring 10, as measured at points of minimum extension near stent valleys 19, and preferably at least 1.5 mm; in the preferred embodiment described and illustrated, this extension is about 1.7 mm and could be made longer at the expense of greater height of the valve.

In the preferred embodiment, stent 14 is provided with a collar 17 to support the upstream end of conduit 21 and its cuff 23, and to resist possible inwardly-directed forces due to tissue regrowth. In applications where such functions may not be needed, such a collar may not be required, and the conduit may simply be extended unsupported to achieve the necessary extension beyond the face of the suture ring.

In the described and illustrated preferred embodiment, suture ring 10 is affixed to stent 14 by a groove and flange on the latter. Alternatively, suture ring 10 could be configured with an inwardly-directed U-shaped cross-section engaging and enveloping a flange on the stent. Or the inner surface of suture ring 10 could be adhesively bonded to body 11 through additional fenestrations through stent 14 to conduit 21. Further, the circular form of fenestrations 20 could be replaced by other forms such as rounded-corner triangles. And, while we prefer to affix the conduit to the stent by material passing through the fenestations, it must be understood that other means may be employed, such as adhesive bonding, interengaged grooves and flanges, and the like. Also, wile the preferred embodiment employs three flexible leaflets, other numbers of leaflets may be employed.

Still other changes may be made in the construction of a prosthetic heart valve of this type without departing from the teaching of this invention, as defined in the following claims.

We claim:

1. A prosthetic heart valve that inhibits chronic thrombus formation and tissue overgrowth, said valve having upstream and downstream ends and including a suture ring which surrounds and supports a generally cylindrical valve body which, in turn, supports a plurality of flexible valve leaflets, said heart valve also comprising an extension of the valve body upstream from the suture ring, said upstream extension extending at least about 1.5 mm to about 3.6 mm upstream and an extension of the valve body downstream from said suture ring, said downstream extension extending about 1.0 mm to about 1.7 mm so as to inhibit chronic thrombus formation and tissue overgrowth from said suture ring around said upstream end of said body to the interior of said body.

* * * * *